United States Patent
Isshiki

(10) Patent No.: US 12,201,294 B2
(45) Date of Patent: Jan. 21, 2025

(54) SLIP KNOT SUTURE CONSTRUCT

(71) Applicant: ConMed Corporation, Largo, FL (US)

(72) Inventor: Ryo Isshiki, Largo, FL (US)

(73) Assignee: ConMed Corporation, Largo, FL (US)

( * ) Notice: Subject to any disclaimer, the term of this patent is extended or adjusted under 35 U.S.C. 154(b) by 0 days.

(21) Appl. No.: 18/588,111

(22) Filed: Feb. 27, 2024

(65) Prior Publication Data

US 2024/0188955 A1 Jun. 13, 2024

Related U.S. Application Data

(62) Division of application No. 17/193,290, filed on Mar. 5, 2021, now Pat. No. 11,911,024.

(60) Provisional application No. 62/986,205, filed on Mar. 6, 2020.

(51) Int. Cl.
*A61B 17/06* (2006.01)

(52) U.S. Cl.
CPC .............. *A61B 17/06166* (2013.01)

(58) Field of Classification Search
CPC ................................. A61B 17/06166
See application file for complete search history.

(56) References Cited

U.S. PATENT DOCUMENTS

| | | | | |
|---|---|---|---|---|
| 2,012,776 A * | 8/1935 | Roeder | ............ | A61B 17/12013 606/139 |
| 4,711,476 A * | 12/1987 | Hanson | ............ | B65H 69/04 289/1.5 |
| 5,129,912 A * | 7/1992 | Noda | ............ | A61B 17/0469 606/147 |
| 5,405,352 A * | 4/1995 | Weston | ............ | A61B 17/0469 606/139 |
| 5,728,109 A * | 3/1998 | Schulze | ............ | A61B 17/0483 606/139 |
| 2006/0293709 A1* | 12/2006 | Bojarski | ............ | A61B 17/0401 606/232 |
| 2011/0270278 A1* | 11/2011 | Overes | ............ | A61B 17/0487 606/228 |
| 2016/0000421 A1* | 1/2016 | Larsen | ............ | A61B 17/0401 606/228 |

* cited by examiner

*Primary Examiner* — Alexander J Orkin
(74) *Attorney, Agent, or Firm* — Bond, Schoeneck & King, PLLC; Frederick J. M. Price

(57) ABSTRACT

A slip knot suture construct system and method for securing multiple limbs of suture. The system includes a suture construct having a length of suture including a standing limb with a standing terminal end and a closing limb with a closing terminal end. The suture construct has three loops: a primary loop formed in the closing limb, the primary loop and closing limb extending to the standing limb, a secondary loop formed in the standing limb, and a locking loop formed in the length of suture between the primary loop and the secondary loop. A limb of suture extends through the primary loop. The limb of suture is secured in the suture construct by pulling the closing terminal end proximally, which pulls the primary loop holding the limb of suture through the locking loop and at least partially into the secondary loop.

4 Claims, 3 Drawing Sheets

SLIP KNOT SUTURE CONSTRUCT

CROSS-REFERENCE TO RELATED APPLICATION

The present application is a division of U.S. patent application Ser. No. 17/193,290, filed Mar. 5, 2021, which claims priority to and the benefit of U.S. Provisional Patent Application No. 62/986,205, filed on Mar. 6, 2020, and entitled "Slip Knot Suture Construct," the entirety of which is incorporated herein by reference.

BACKGROUND OF THE INVENTION

1. Field of the Invention

The present invention relates to a surgical fixation construct and, more particularly, to a slip knot suture construct system and method for securing multiple limbs of suture.

2. Description of Related Art

Surgical procedures, particularly arthroscopic procedures, often require knot tying. Knot tying is useful for securing suture anchors, fixing the relative positions of soft tissue, and/or attaching a graft. There are many types of knots and knot tying methods that result in cumbersome knots or one-way knots. Cumbersome knots can irritate the area at or around the surgical site, which can lead to additional trauma to the patient. One-way knots only function in one direction, i.e., only tighten the knot. Thus, one-way knots cannot be loosened if repositioning of the suture anchor, soft tissue, or graft is necessary.

Therefore, there is a need for a simplified, adjustable (two-way) knot for use in arthroscopic surgical procedures.

The term "suture" as used herein may be any type of filamentous material such as a biocompatible or bioabsorbable filament, ribbon, tape, woven or non-woven material.

Description of the Related Art Section Disclaimer: To the extent that specific patents/publications/products are discussed above in this Description of the Related Art Section or elsewhere in this disclosure, these discussions should not be taken as an admission that the discussed patents/publications/products are prior art for patent law purposes. For example, some or all of the discussed patents/publications/products may not be sufficiently early in time, may not reflect subject matter developed early enough in time and/or may not be sufficiently enabling so as to amount to prior art for patent law purposes. To the extent that specific patents/publications/products are discussed above in this Description of the Related Art Section and/or throughout the application, the descriptions/disclosures of which are all hereby incorporated by reference into this document in their respective entirety(ies).

BRIEF SUMMARY OF THE INVENTION

Embodiments of the present invention are directed to a slip knot suture construct system and method for securing multiple limbs of suture. According to an aspect, the present invention is a suture construct. An embodiment of the suture construct includes a length of suture comprising a standing limb with a standing terminal end and a closing limb with a closing terminal end, a primary loop formed in the closing limb, the primary loop and closing limb extending to the standing limb, a secondary loop formed in the standing limb, and a locking loop formed in the length of suture between the primary loop and the secondary loop.

According to another aspect, the present invention is a suture construct system. The system includes a suture construct having a length of suture including a standing limb with a standing terminal end and a closing limb with a closing terminal end. The suture construct has three loops: a primary loop formed in the closing limb, the primary loop and closing limb extending to the standing limb, a secondary loop formed in the standing limb, and a locking loop formed in the length of suture between the primary loop and the secondary loop. A limb of suture extends through the primary loop.

According to another aspect, the present invention is a method for creating a suture construct and securing a limb of suture therein. The method includes the steps of: (i) providing a length of suture comprising a standing limb with a standing terminal end and a closing limb with a closing terminal end; (ii) forming a primary loop in the closing limb such that standing limb extends from the primary loop and closing limb; (iii) wrapping the standing limb around itself and the closing limb, forming a secondary loop in the standing limb; (iv) passing the standing limb around the primary loop, forming a locking loop in the standing limb; and (v) passing the standing limb through the secondary loop at least twice.

These and other aspects of the invention will be apparent from and elucidated with reference to the embodiment(s) described hereinafter.

BRIEF DESCRIPTION OF THE SEVERAL VIEWS OF THE DRAWING(S)

The present invention will be more fully understood and appreciated by reading the following Detailed Description in conjunction with the accompanying drawings. The accompanying drawings illustrate only typical embodiments of the disclosed subject matter and are therefore not to be considered limiting of its scope, for the disclosed subject matter may admit to other equally effective embodiments. Reference is now made briefly to the accompanying drawings, in which.

DETAILED DESCRIPTION OF THE INVENTION

Aspects of the present invention and certain features, advantages, and details thereof, are explained more fully below with reference to the non-limiting examples illustrated in the accompanying drawings. Descriptions of well-known structures are omitted so as not to unnecessarily obscure the invention in detail. It should be understood, however, that the detailed description and the specific non-limiting examples, while indicating aspects of the invention, are given by way of illustration only, and are not by way of limitation. Various substitutions, modifications, additions, and/or arrangements, within the spirit and/or scope of the underlying inventive concepts will be apparent to those skilled in the art from this disclosure.

Figure 1:
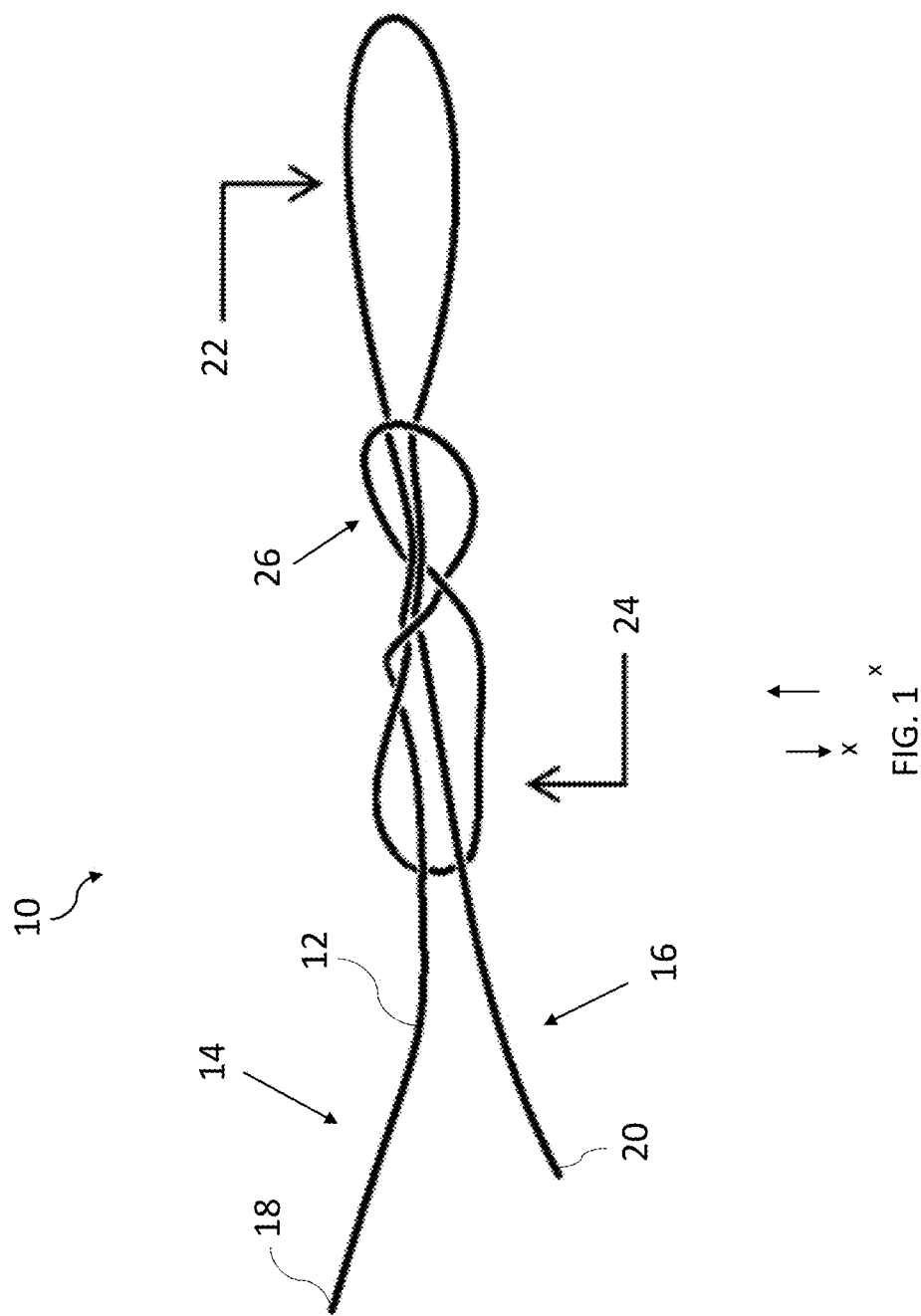
FIG. 1 is a top view of a suture construct in a pre-deployment configuration, according to an embodiment.

Referring now to the figures, wherein like reference numerals refer to like parts throughout, FIG. 1 is a top view of a suture construct 10 in a pre-deployment configuration, according to an embodiment. The suture construct 10 is comprised of a length of suture 12. The length of suture 12 includes a standing limb 14 connected to a closing limb 16. The standing limb 14 has a standing terminal end 18 and the closing limb 16 has a closing terminal end 20. The length of suture 12 has a primary loop 22 and a secondary loop 24 formed therein between the standing terminal end 18 and the closing terminal end 20.

The primary loop 22 is the distalmost portion of the suture construct 10. Primary loop 22 is formed by the closing limb 16. The standing limb 14 extends from the primary loop 22 (and the closing limb 16). From the primary loop 22, the standing limb 14 is wrapped around itself and the closing limb 16, forming the secondary loop 24. As shown in FIG. 1, the secondary loop 24 encircles the standing limb 14 and the closing limb 16.

From the secondary loop 24, the standing limb 14 is passed around the primary loop 22, forming a locking loop 26. The locking loop 26 is between the primary loop 22 and the secondary loop 24, as shown in FIG. 1. The secondary loop 24 is the proximal most loop in the suture construct 10. From the locking loop 26, the standing limb 14 is passed through the secondary loop 24 twice. The resulting suture construct 10, in the pre-deployment configuration, has the standing limb 14 and closing limb 16 extending proximally from the secondary loop 24 with the locking loop 26 between the secondary loop 24 and the distal primary loop 22. The suture construct 10 functions like a modified slip knot, as described in detail below.

Figure 2:
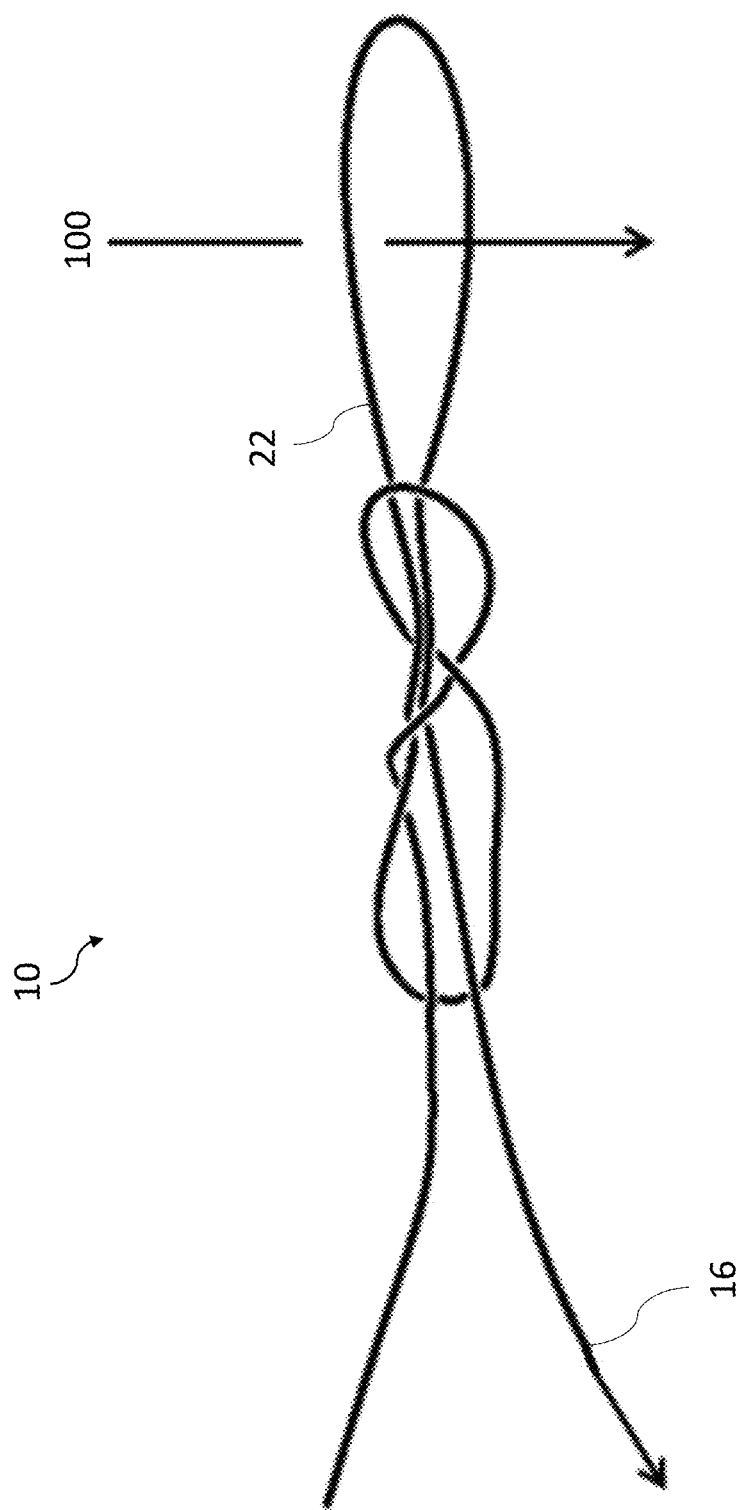
FIG. 2 is a top view of a suture construct in a loading configuration, according to an embodiment.

FIG. 2 is a top view of a suture construct 10 in a loading configuration, according to an embodiment. In the loading configuration, one or more limbs of suture 100 are loaded onto the suture construct 10. The one or more limbs of suture 100 are passed through the primary loop 22, as shown in FIG. 2. To hold and secure the one or more limbs of suture 100, the closing limb 16 is pulled in the proximal direction, which collapses the primary loop 22 around the one or more limbs of suture 100.

Figure 3:
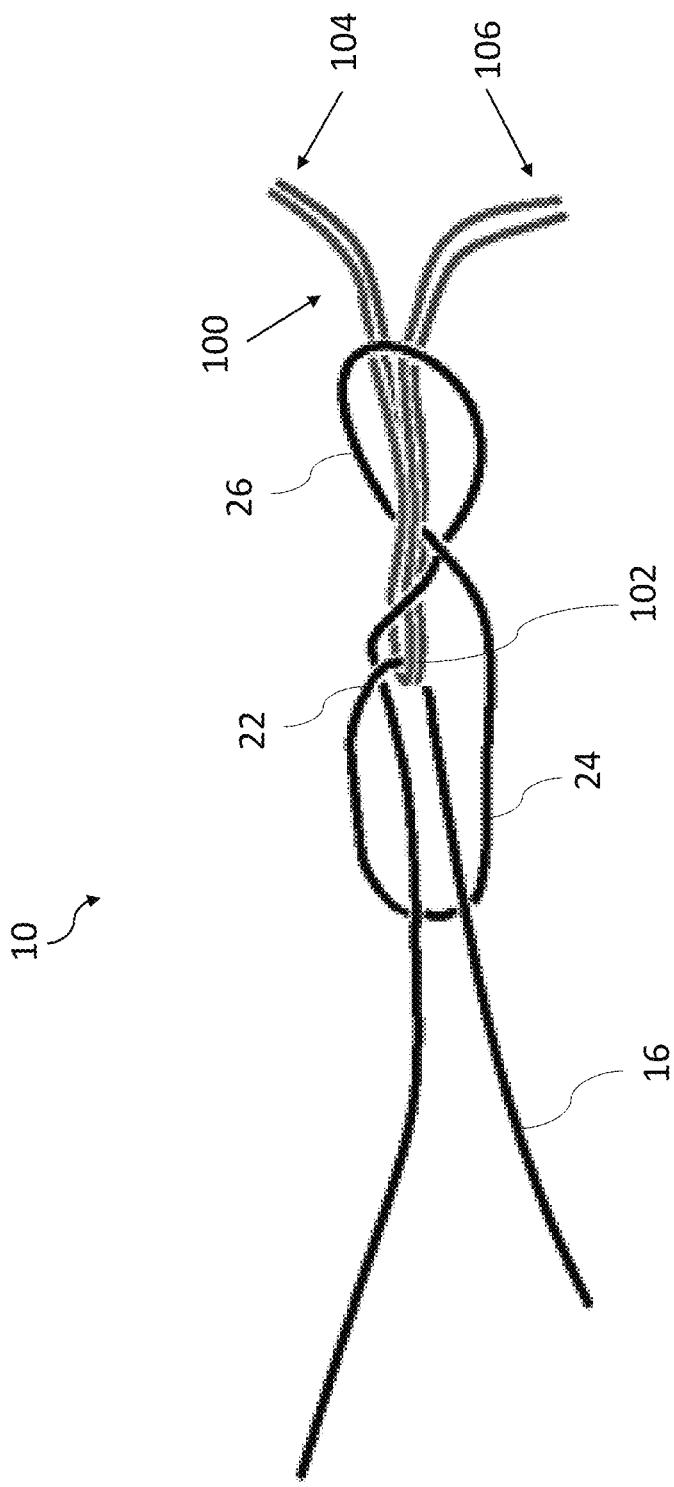
FIG. 3 is a top view of a suture construct in the post-deployment configuration, according to an embodiment.

FIG. 3 is a top view of a suture construct 10 in the post-deployment configuration, according to an embodiment. If additional tension is added to the closing limb 16, i.e., if the closing limb 16 is pulled farther in the proximal direction, the primary loop 22 (holding the one or more limbs of suture 100) is pulled through the locking loop 26 and into the secondary loop 24, as shown in FIG. 3. In the post-deployment configuration of the suture construct 10, the suture construct 10 is inverted. This inversion introduces a bend 102 in the one or more limbs of suture 100.

As shown in FIG. 3, the tight bend 102 in the one or more limbs of suture 100 essentially folds the one or more limbs of suture 100 such that first tails 104 and second tails 106 of the one or more limbs of suture 100 extend distally from the locking loop 26. The depicted embodiment shows two limbs of suture 100, each bent or folded to have a first tail 104 and a second tail 106. However, the suture construct 10 can accommodate any number of limbs of suture 100. The limb(s) of suture 100 may originate from a suture strand that is separate and distinct from the suture construct 10 or the limb of suture 100 can be the standing limb 14 of the suture construct 10 itself.

To secure the limbs of suture 100 within the suture construct 10, the closing limb 16 is pulled again in the proximal direction. By tensioning or pulling the closing limb 16 again, the locking loop 26 closes (i.e., decreases or collapses) around the limbs of suture 100, holding them in place. However, the locking loop 26 can be reopened by adding slack to the closing limb 16. Therefore, the locking loop 26 allows the suture construct 10 to function as a two-way, adjustable knot.

It should be understood that the values used above are only representative values, and other values may be in keeping with the spirit and intention of this disclosure.

While several inventive embodiments have been described and illustrated herein with reference to certain exemplary embodiments, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein (and it will be understood by one skilled in the art that various changes in detail may be effected therein without departing from the spirit and scope of the invention as defined by claims that can be supported by the written description and drawings). More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto; inventive embodiments may be practiced otherwise than as specifically described and claimed. Further, where exemplary embodiments are described with reference to a certain number of elements it will be understood that the exemplary embodiments can be practiced utilizing either less than or more than the certain number of elements.

All references, including publications, patent applications, and patents, cited herein are hereby incorporated by reference to the same extent as if each reference were individually and specifically indicated to be incorporated by reference and were set forth in its entirety herein.

All definitions, as defined and used herein, should be understood to control over dictionary definitions, definitions in documents incorporated by reference, and/or ordinary meanings of the defined terms.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if not directly attached to where there is something intervening.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

Approximating language, as used herein throughout the specification and claims, may be applied to modify any quantitative representation that could permissibly vary without resulting in a change in the basic function to which it is related. Accordingly, a value modified by a term or terms, such as "about" and "substantially", are not to be limited to the precise value specified. In at least some instances, the approximating language may correspond to the precision of an instrument for measuring the value. Here and throughout the specification and claims, range limitations may be combined and/or interchanged; such ranges are identified and include all the sub-ranges contained therein unless context or language indicates otherwise.

The recitation of ranges of values herein are merely intended to serve as a shorthand method of referring individually to each separate value falling within the range, unless otherwise indicated herein, and each separate value is incorporated into the specification as if it were individually recited herein.

All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not impose a limitation on the scope of the invention unless otherwise claimed.

No language in the specification should be construed as indicating any non-claimed element as essential to the practice of the invention.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

It will be apparent to those skilled in the art that various modifications and variations can be made to the present invention without departing from the spirit and scope of the invention. There is no intention to limit the invention to the specific form or forms disclosed, but on the contrary, the intention is to cover all modifications, alternative constructions, and equivalents falling within the spirit and scope of the invention, as defined in the appended claims. Thus, it is intended that the present invention cover the modifications and variations of this invention provided they come within the scope of the appended claims and their equivalents.

What is claimed is:

1. A method for creating a suture construct and securing a limb of suture therein, comprising the steps of:
    providing a length of suture comprising a standing limb with a standing terminal end and a closing limb with a closing terminal end;
    forming a primary loop in the closing limb such that standing limb extends from the primary loop and closing limb;
    wrapping the standing limb around itself and the closing limb, forming a secondary loop in the standing limb;
    passing the standing limb around the primary loop, forming a locking loop in the standing limb;
    passing the standing limb through the secondary loop at least twice;
    passing one or more limbs of suture through the primary loop, and
    pulling the closing terminal end proximally, which pulls the primary loop through the locking loop and into the secondary loop to collapse the primary loop around the one or more limbs of suture to secure the one or more limbs of suture.

2. The method of claim 1, wherein the step of pulling the closing terminal end proximally pulls at least a portion of the one or more limbs of suture into the secondary loop via the primary loop.

3. The method of claim 2, further comprising a bend in the limb of suture in the portion of the limb of suture in the secondary loop.

4. The method of claim 3, further comprising a first tail and a second tail of the limb of suture extending distally from the bend.

* * * * *